US00PP10933P

United States Patent [19]

Kordes

[11] Patent Number: Plant 10,933

[45] Date of Patent: Jun. 1, 1999

[54] PICEA GLAUCA PLANT NAMED 'BLUE WONDER'

[75] Inventor: Günter Kordes, Bilsen, Germany

[73] Assignee: Jeddeloh Farms, Gresham, Oreg.

[21] Appl. No.: 08/887,983

[22] Filed: Jul. 3, 1997

[51] Int. Cl.[6] ..... A01H 7/00

[52] U.S. Cl. ..... Plt./213

[58] Field of Search ..... Plt./50.1

[56] References Cited

PUBLICATIONS

GTITIM UPOVROM Citation for 'Bluewonder' as per DE PBR FI 00005; Mar. 4, 1991.

*Primary Examiner*—Douglas W. Robinson
*Assistant Examiner*—Kent L. Bell
*Attorney, Agent, or Firm*—C. A. Whealy

[57] ABSTRACT

A distinct cultivar of Picea plant named 'Blue Wonder', characterized by its blue-green colored needles; compact plant habit; slow growth rate; and low vigor.

2 Drawing Sheets

The present invention relates to a new and distinct cultivar of Picea plant, botanically known as *Picea glauca* and referred to by the cultivar name 'Blue Wonder'.

The new cultivar was discovered by the inventor in Siegerkreis, Germany, as a naturally-occurring mutation of the nonpatented *Picea glauca* cultivar 'Conica' and was observed in a group of plants of the parent cultivar in 1984.

Asexual reproduction of the new cultivar by terminal cuttings taken in a controlled environment in Bilsen, Germany, has shown that the unique features of this new Picea are stable and reproduced true to type in successive generations.

The cultivar 'Blue Wonder' has not been observed under all possible environmental conditions. The phenotype may vary somewhat with variations in environment such as temperature, light intensity and fertility level, without, however, any variance in genotype.

The following traits have been repeatedly observed and are determined to be the unique characteristics of 'Blue Wonder'. These characteristics in combination distinguish 'Blue Wonder' as a new and distinct cultivar;

1. Blue-green colored needles.
2. Compact plant habit.
3. Slow growth rate and low vigor.

Compared to plants of the parent cultivar, *Picea glauca* 'Conica', plants of the new cultivar are more compact, have blue needles and are slower growing. Compared to plants of the new cultivar, other blue-needled cultivars, such as 'Sander's Blue' and 'Arneson's Blue' (neither patented), have lighter blue needles, are taller, grow faster, and tend to revert to their green-needled form. A comparison of the needle color for the new cultivar and the cultivars 'Sander's Blue' and 'Arneson's Blue' appears in Chart A at the end of the specification.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a top perspective view of a typical plant of 'Blue Wonder'.

The photograph on the second sheet comprises a side perspective view of three typical containerized plants of 'Blue Wonder'. The foliage color in the photographs may differ from actual color due to wet growing conditions.

DETAILED BOTANICAL DESCRIPTION

In the following description, color references are made to The Royal Horticultural Society Colour Chart except where general terms of ordinary dictionary significance are used. The following observations and measurements describe plants grown in Bilsen, Germany, under commercial field practice.

Botanical classification: *Picea glauca* cultivar 'Blue Wonder'.

Parentage: Naturally-occurring mutation of nonpatented *Picea glauca* cultivar 'Conica'.

Propagation:

*Type.*—Cuttings.

*Time to develop roots.*—About six months.

*Rooting habit.*—Fine, fibrous.

Plant description:

*Appearance.*—Perennial woody shrub. Plants upright, conical, compact and freely banching.

*Vigor/plant size.*—Very slow-growing, low vigor. During the 3rd and 5th growing season, plants grow about 6 to 8 cm per year; after the 5th year, plants grow about 8 to 20 cm per year. Plants attain a height of about 2 meters with a basal diameter of about 75 cm after about 18 years of growth.

*Stem description.*—Main trunk: Smooth, 199D in color. Branching habit: Very freely branching. Lateral branch attachment: Lower lateral branches angled about 30 to 45° from the horizontal; towards the plant apex, branch angles become narrower, about 80° from the horizontal. Lateral branch color: 173D.

*Foliage description.*—Leaf arrangement: Rosette, compound, sessile. Leaf shape: Needle, acicular, four-angled. Leaf apex: Acute. Leaf margin: Entire. Leaf texture: Smooth. Leaf size, fully expanded: Length: 1 to 1.2 cm. Width: About 0.5 mm. Color: Young foliage, both surfaces: Light green, with bluish, 119C, bloom. Under wet conditions, new leaves are more green. Mature foliage, both surfaces: Green, close to 139A, with bluish, 121A, bloom. Under wet conditions, mature leaves are more green.

Flowering description: Inconspicuous, not notable, cone formation has not been observed.

Disease resistance: The new Picea has not exhibited any notable resistance nor susceptibility to diseases commonly observed on species of Picea.

CHART A

| CHARACTERISTIC | 'BLUE WONDER' | 'SANDER'S BLUE' | 'ARNESON'S BLUE' |
|---|---|---|---|
| YOUNG LEAF COLOR, UPPER SURFACE | 120B | 120C | 119D |
| YOUNG LEAF COLOR, LOWER SURFACE | 120B | 120C | 199D |

CHART A-continued

| CHARACTERISTIC | 'BLUE WONDER' | 'SANDER'S BLUE' | 'ARNESON'S BLUE' |
|---|---|---|---|
| MATURE LEAF COLOR, UPPER SURFACE | 121A | 121B | 121C |
| MATURE LEAF COLOR, LOWER SURFACE | 121A | 121B | 121C |

It is claimed:

1. A new and distinct cultivar of Picea plant named 'Blue Wonder', as illustrated and described.

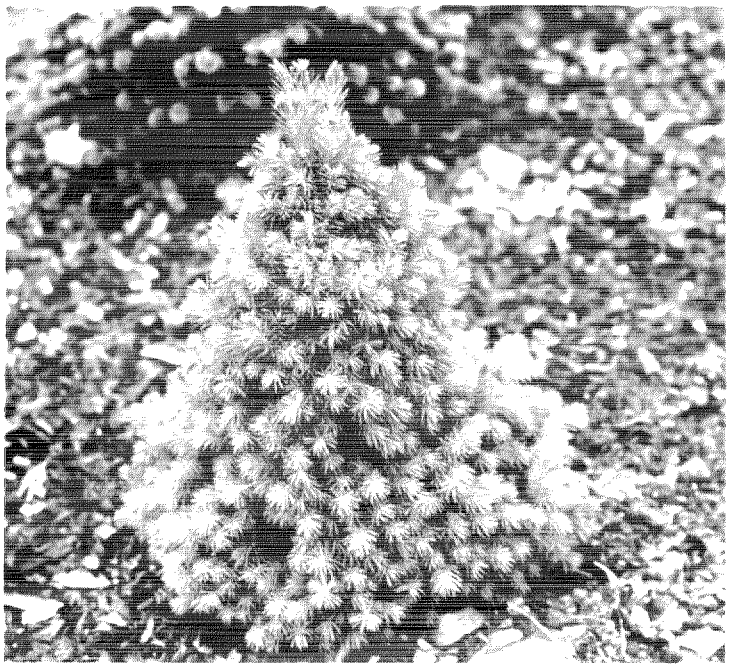

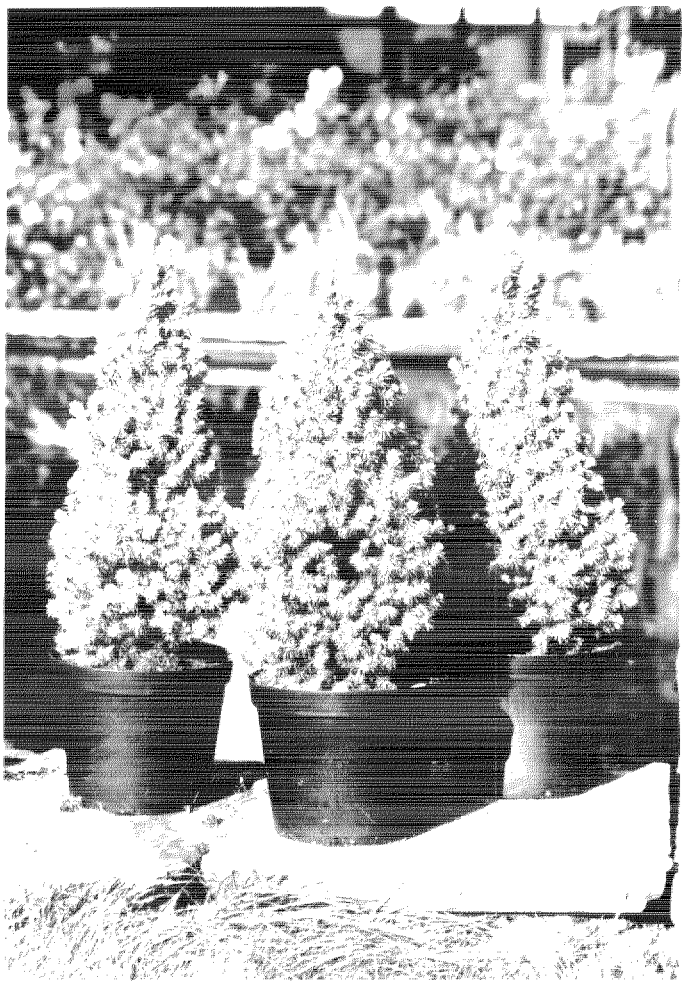

* * * * *